United States Patent [19]

Saiki et al.

[11] Patent Number: 5,273,883
[45] Date of Patent: Dec. 28, 1993

[54] METHODS AND REAGENTS FOR γ-GLOBIN TYPING

[75] Inventors: Randall K. Saiki, Richmond; Shanavaz L. Nasarabadi, Fremont, both of Calif.

[73] Assignee: Hoffmann-La Roche Inc., Nutley, N.J.

[21] Appl. No.: 977,694

[22] Filed: Nov. 17, 1992

Related U.S. Application Data

[62] Division of Ser. No. 696,793, May 7, 1991.

[51] Int. Cl.$^5$ .............................................. C12Q 1/68
[52] U.S. Cl. ........................................ 435/6; 935/77; 935/78
[58] Field of Search .................. 435/6, 91; 935/77, 78

[56] References Cited

U.S. PATENT DOCUMENTS

| 4,683,194 | 7/1987 | Saiki et al. | 435/6 |
| 4,683,195 | 7/1987 | Mullis et al. | 435/6 |
| 4,965,188 | 10/1990 | Mullis et al. | 435/6 |

FOREIGN PATENT DOCUMENTS

8911548 11/1989 PCT Int'l Appl. .

OTHER PUBLICATIONS

Jeffreys, 1979, Cell 18:1-10, "DNA Sequence Variants in the G-Gamma-, A-Gamma-, Delta-and Beta-Globin Genes of Man".

Slightom et al., 1980, Cell 21:627-638, "Human Feta G-Gamma-and A-Gamma-Globin Gene: Complete Nucleotide Sequences Suggest that DNA can be Exchanged Between These Duplicate Genes".

Shiokawa et al., 1989, J. Biochem. 105:184-189, "Heterogeneity of the Gamma-Globin Gene Sequences in Japanese Individuals: Implication of Gene Conversion in Generation of Polymorphisms".

Cui et al., 1989, Proc. Natl. Acad. Sci. USA 86:9389-9393, "Single-Sperm Typing: Determination of Genetic Distance Between the G-Gamma-Globin and Parathyroid Hormone loci by Using the Polymerase Chain Reaction and Allele-Specific Oligomers".

Higuchi et al., 1988, Nature 332:543-546, "DNA Typing From Single Hairs".

Li et al., 1988, Nature 335:414-417, "Amplification and Analysis of DNA Sequences in Single Human Sperm and Diploid Cells".

Reynolds and Sensabaugh, 1991, Anal. Chem. 63:2-15, "Analysis of Genetic Markers in Forensic DNA Samples Using the Polymerase Chain Reaction".

Saiki et al., 1989, Proc. Natl. Acad. Sci. USA 86:6230-6234, "Genetic Analysis of Amplified DNA With Immobilized Sequence-Specific Oligonucleotide Probes".

AmpliType DQalpha DNA Typing Kit Package Insert.

*Primary Examiner*—Stephanie W. Zitomer
*Attorney, Agent, or Firm*—George M. Gould; Dennis P. Tramaloni; Stacey R. Sias

[57] ABSTRACT

Methods and reagents for determining an individual's genotype at the $^G$γ-globin locus with respect to a set of three alleles using sequence-specific oligonucleotide probes enable one to type samples from a variety of sources, including samples comprising RNA or cDNA templates, and can be applied to nucleic acids in which a target region spanning the polymorphism has first been amplified. This three-allele system facilitates typing tissue for determining individual identity and has application in the field of forensic science.

10 Claims, No Drawings

METHODS AND REAGENTS FOR γ-GLOBIN TYPING

This application is a divisional of application Ser. No. 07/696,793, filed May 7, 1991.

BACKGROUND OF THE INVENTION

1. Field of the Invention

The present invention provides methods and reagents for determining an individual's genotype at the $^G\gamma$-globin locus with respect to a set of three alleles using sequence-specific oligonucleotide probes. The invention enables one to type samples from a variety of sources, including samples comprising RNA or cDNA templates, and can be applied to amplified nucleic acids containing the target polymorphic region. The three-allele system provides substantially more information than the prior art bi-allelic system based on the polymorphic HindIII site. The present typing system facilitates typing tissue for determining individual identity and is especially useful in the field of forensic science.

2. Description of Related Art

The β-related globin proteins are encoded by genes on the short arm of human chromosome 11. The $^G\gamma$-globin and $^A\gamma$-globin genes respectively code for the $^G\gamma$- and $^A\gamma$-polypeptide chains of $\alpha_2{}^G\gamma_2$ and $\alpha_2{}^A\gamma_2$, the major species of fetal hemoglobin produced by the fetal liver. The β- and δ-globin genes are activated around birth, while the two γ-globin genes are inactivated. The two adult hemoglobins, produced in the bone marrow, are $\alpha_2\beta_2$ and $\alpha_2\delta_2$. The nucleotide sequences of the $^G\gamma$-globin and $^A\gamma$-globin genes were first described by Slightom et al., 1980, *Cell* 21:627–638. Each gene consists of three exons and two intervening sequences (IVS).

The $^G\gamma$-globin and $^A\gamma$-globin genes have been classified by variant patterns of restriction endonuclease cleavage site number and location. In particular, a HindIII site polymorphism has been discovered (Jeffreys, 1979, *Cell* 18:1–10) near the 3' end of the second IVS.

Nucleotide sequence variability corresponding to the HindIII site polymorphism has been observed in the study of gene conversion in the two fetal globin genes (Shiokawa et al., 1989, *J. Biochem.* 105:184–189, incorporated herein by reference). Probes for the sequences corresponding to the HindIII polymorphism have been used in a study of linkage between the $^G\gamma$-globin and parathyroid loci (Cui et al., 1989, *Proc. Natl. Acad. Sci.* 6:9389–9393). In both of these studies, the observed HindIII site polymorphism corresponds to the present A and B alleles.

Identification of individuals is possible with genetic typing. The use of polymerase chain reaction (PCR) amplification and nucleotide probes to detect even single nucleotide changes in a gene sequence has revolutionized the field of forensic serology (see Reynolds and Sensabaugh 1991, *Anal. Chem.* 63:2–15). With PCR and other nucleic acid amplification methods, DNA typing can now be done with samples that contain insufficient DNA for typing by any other means; single hairs, for example, provide enough DNA for PCR-based DNA typing. (Higuchi et al., 1988, Nature 332:543–546).

SUMMARY OF INVENTION

The present invention provides methods and reagents for determining an individual's genotype at the $^G\gamma$-globin locus with respect to a set of three alleles. Only two alleles, defined by a HindIII restriction enzyme cleavage site polymorphism, have been described in the prior art. The discovery of a third allele and the creation of sequence-specific, oligonucleotide probes complementary to the three alleles form the basis of the present invention, which provides a relatively rapid, convenient, and accurate genotyping method. In this tri-allelic system, allele A corresponds to the allele containing the HindIII site (+HindIII), whereas alleles B and C subdivide the class of alleles lacking the HindIII site (−HindIII) into two distinct alleles. The specific sequences defining the A, B, and C alleles are provided below.

One aspect of the invention relates to a process for determining an individual's genotype at the $^G\gamma$-globin locus from a sample containing nucleic acid obtained from the individual. The process comprises hybridizing the sample nucleic acid with a panel of sequence-specific oligonucleotide (SSO) probes; each of the probes is complementary to a variant segment of the $^G\gamma$-globin locus defining the A, B, or C allele. The hybridization is carried out under conditions such that the SSO probes bind to the nucleic acid to form stable hybrid duplexes only if the hybridizing region of each of the probes is exactly complementary to the nucleic acid. The hybrids formed between the nucleic acid and the SSO probes can then be detected. The sample can contain amplified nucleic acids, so long as the relevant regions of nucleic acid have been amplified; any of the known methods for increasing the copy number of a region of nucleic acid in vitro can be used to amplify the nucleic acid.

Another aspect of the invention relates to SSO probes useful for discriminating between the three alleles that may be present in the sample.

A third aspect of the invention relates to kits useful for determining the $^G\gamma$-globin genotype of an individual. These kits take a variety of forms and comprise one or more SSO probes and, in one embodiment, comprise a panel of probes sufficient to determine the $^G\gamma$-globin genotype relative to the A, B, and C alleles and instructions for determining the genotype by using the kit ingredients. The kits can also comprise one or more amplification reagents, e.g., primers, polymerase, buffers, and nucleoside triphosphates.

A fourth aspect of the invention relates to forensic methods to determine the probable origin of a biological sample. The present three-allele system substantially improves the discriminative power of $^G\gamma$-globin DNA typing methodology and will have an important impact on forensic methodology.

To aid in understanding the invention, several terms are defined below.

The terms "$^G\gamma$-globin gene" and "$^G\gamma$-globin locus" refer to a transcribed region of DNA that contains the coding sequence for the $^G\gamma$-globin protein and the untranslated intervening sequences.

The term "alleles" refers to variants of the nucleotide sequence of a gene. An allele is defined by the presence of a specific subsequence. An allele may consist of a set of sequence variants, all of which contain the specific subsequence that defines the allele.

The term "allele A" refers to sequence variants of the $^G\gamma$-globin gene that contain the HindIII restriction enzyme cleavage site sequence 5'-AAGCTT.

The term "allele B" refers to sequence variants of the $^G\gamma$-globin gene that contain the sequence 5'-AAGCTG in place of the HindIII restriction site of allele A.

The term "allele C" refers to sequence variants of the $^G\gamma$-globin gene that contain the sequence 5'-AATCTT in place of the HindIII restriction site of allele A.

The term "genotype" refers to a description of the alleles of a gene contained in an individual or a sample.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066.

The terms "polymorphic" and "polymorphism" refer to the condition in which two or more variants of a specific DNA sequence can be found in a population.

The terms "polymorphic gene" and "polymorphic region" refer to that region of the DNA where a polymorphism occurs.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template.

The term "primer" may refer to more than one primer, particularly in the case where there is some ambiguity in the information regarding one or both ends of the target region to be amplified. For instance, if a nucleic acid sequence is inferred from a protein sequence, a "primer" is actually a collection of primer oligonucleotides containing sequences representing all possible codon variations based on the degeneracy of the genetic code. One of the primers in this collection will be homologous with the end of the target sequence. Likewise, if a "conserved" region shows significant levels of polymorphism in a population, mixtures of primers can be prepared that will amplify adjacent sequences. A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISAS), biotin, or haptens and proteins for which antisera or monoclonal antibodies are available. A label can also be used to "capture" the primer, so as to facilitate the immobilization of either the primer or a primer extension product, such as amplified DNA, on a solid support.

The terms "restriction endonucleases" and "restriction enzymes" refer to enzymes, usually of bacterial origin, that cut double-stranded DNA at or near a specific nucleotide sequence.

The terms "sequence-specific oligonucleotide" and "SSO" refer to oligonucleotides that have a sequence, called a "hybridizing region," exactly complementary to the sequence to be detected, typically sequences characteristic of a particular allele, which under "sequence-specific, stringent hybridization conditions" will hybridize only to that exact complementary target sequence. Depending on the sequences being analyzed, one or more sequence-specific oligonucleotides may be employed for each sequence. The terms "probe" and "SSO probe" are used interchangeably with SSO.

The term "target region" refers to a region of a nucleic acid which is to be analyzed and usually includes a polymorphic region.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3'-end of the primer and proceeds in the direction toward the 5' end of the template until synthesis terminates. A purified thermostable polymerase enzyme is described more fully in U.S. Pat. No. 4,889,818, incorporated herein by reference, and is commercially available from Perkin-Elmer Cetus Instruments (PECI, Norwalk, Conn.).

DETAILED DESCRIPTION OF THE INVENTION

The present invention provides processes and reagents for determining the $^G\gamma$-globin genotype of an individual. In part, the invention results from the discovery of an additional polymorphism in the region specifying the HindIII site. This additional polymorphism was first observed after screening polymerase chain reaction (PCR) amplified DNA containing the polymorphic region of the $^G\gamma$-globin the presence or absence of the HindIII site with sequence-specific oligonucleotide probes. A significant fraction of the samples from Black individuals did not hybridize to either probe, indicating that these individuals were homozygous for an unknown allele. The existence of this third allele was confirmed by direct sequencing of the PCR products from the above amplification. The defining sequences for these three alleles, here designated alleles A, B, and C, are provided above. The SSO probes provided by the invention enable one to detect the variant genotypes by inference from the pattern of binding of a panel of probes. In a preferred embodiment, each probe of the panel is specific for a different allele of the $^G\gamma$-globin gene. Table VI provides designations of illustrative probes of the invention; the corresponding sequences are provided in the sequence listing section.

As described above, the A, B, and C alleles of the $^G\gamma$-globin gene can be distinguished from one another by the polymorphic sequence corresponding to the HindIII site of the A allele. In an alternative embodiment of the invention, however, one can distinguish certain C alleles from certain A and B alleles by detecting a polymorphism adjacent to the HindIII polymorphism. In all reported sequences for A and B alleles and in all C alleles sequenced by the present inventors, the HindIII polymorphism is contained within the larger sequences shown in Table I below:

TABLE I

| Allele | Sequence |
|---|---|
| A | 5'-AAGCTTGGTGTGTAG-3' (SEQ ID NO: 56) |
| B | 5'-AAGCTGGGTGTGTAG-3' (SEQ ID NO: 57) |
| C | 5'-AATCTTGGTGTGTAA-3' (SEQ ID NO: 58) |

Thus, one can distinguish the C allele shown above from the A and B alleles shown above by use of SSO probes specific for the A:G polymorphism at the 3' end of the sequence. Such probes would typically contain sequences that, in addition to hybridizing to the A:G polymorphic base, would hybridize to sequences 3' to the polymorphic base. Such 3' sequences are not shown in the Table above but can be obtained from Shiokawa et al., supra. There may be C alleles, however, that do not contain this single base variation, but could still be distinguished by SSO probes specific for the HindIII polymorphism.

In a preferred embodiment of the invention, the process for DNA based typing of $^G\gamma$-globin genotype comprises amplifying a nucleic acid sequence which contains the variable portion of a $^G\gamma$-globin gene, determining the variant $^G\gamma$-globin sequence present with SSO probes; and inferring the $^G\gamma$-globin genotype from the pattern of binding of the SSO probes to the amplified target sequence. To facilitate practice of this preferred embodiment, the present invention provides primers for amplifying by a PCR the $^G\gamma$-globin target region. The designations of these primers are listed in Table VII; the sequences of these primers are in the sequence listing section.

In this preferred method, a sample containing nucleic acid is obtained from an individual whose $^G\gamma$-globin genotype is to be determined. Any type of tissue containing $^G\gamma$-globin nucleic acid may be used for purposes of the present invention. Because the genotyping methods of the present invention can utilize amplified nucleic acids, and because the PCR technique can amplify extremely small quantities of nucleic acid, even samples containing only a few copies of the $^G\gamma$-globin gene can be typed for the $^G\gamma$-globin variants by the present method. For instance, even single hair contains enough DNA for purposes of the present invention, as evidenced by the DQαDNA typing methods described by Higuchi et al., supra.

In general, the nucleic acid in the sample will be DNA, most usually genomic DNA. However, the present invention can also be practiced with other nucleic acids, such as messenger RNA or cloned DNA, and the nucleic acid may be either single-stranded or double-stranded in the sample and still be suitable for purposes of the present invention. Those skilled in the art recognize that whatever the nature of the nucleic acid, the nucleic acid can be typed by the present method merely by taking appropriate steps at the relevant stage of the process. If PCR is used to amplify the nucleic acid in the sample, then the sample will usually comprise double-stranded DNA after amplification and before probe hybridization.

As noted above, in a preferred embodiment, the $^G\gamma$-globin typing method and probes of the invention are used in conjunction with PCR-amplified target DNA. Those practicing the present invention should note, however, that amplification of $^G\gamma$-globin target sequences in a sample may be accomplished by any known method, such as ligase chain reaction (LCR), transcription amplification and self-sustained sequence replication, each of which provides sufficient amplification so that the target sequence may be detected by nucleic acid hybridization to an SSO probe. Alternatively, methods which amplify the probe to detectable levels can be used, such as Qβ-replicase amplification. The term "probe" encompasses the sequence-specific oligonucleotides used in the above procedures; for instance, the two or more oligonucleotides used in LCR are "probes" for purposes of the present invention, even though some embodiments of LCR only require ligation of the probes to indicate the presence of an allele.

Although the PCR process is well known in the art (see U.S. Pat. Nos. 4,683,195; 4,683,202; and 4,965,188, each of which is incorporated herein by reference) and although commercial vendors, such as PECI, sell PCR reagents and publish PCR protocols, some general PCR information is provided below for purposes of clarity and full understanding of the invention to those unfamiliar with the PCR process.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids from biological samples are known in the art. For example, see those described in Higuchi et al., 1989 in *PCR Technology* (Enlich ed., Stockton Press, New York). Alternatively, if the sample is fairly readily disruptable, the nucleic acid need not be purified prior to amplification by the PCR technique, i.e., if the sample is comprised of cells, particularly peripheral blood lymphocytes or amniocytes, lysis and dispersion of the intracellular components may be accomplished merely by suspending the cells in hypotonic buffer.

Because the nucleic acid in the sample is first denatured (assuming the sample nucleic acid is double-stranded) to begin the PCR process, and because simply heating some samples results in the disruption of cells, isolation of nucleic acid from the sample can sometimes be accomplished in conjunction with strand separation. Strand separation can be accomplished by any suitable denaturing method, however, including physical, chemical, or enzymatic means. Typical heat denaturation involves temperatures ranging from about 80° C. to 105° C. for times ranging from seconds to about 1 to 10 minutes. Strand separation may also be induced by a helicase, an enzyme capable of exhibiting helicase activity. For example, the enzyme RecA has helicase activity in the presence of ATP. The reaction conditions suitable for strand separation by helicases are known in the art (see Kuhn Hoffman-Berling 1978, *CSH-Quantitative Biology* 43:63-67; and Radding 1982, *Ann. Rev. Genetics* 16:405-436).

As noted above strand separation may be accomplished in conjunction with the isolation of the sample nucleic acid or as a separate step. In the preferred embodiment of the PCR process, strand separation is achieved by heating the reaction to a sufficiently high temperature for an effective time to cause the denaturation of the duplex, but not to cause an irreversible denaturation of the polymerase (see U.S. Pat. No. 4,965,188). No matter how strand separation is achieved, however, once the strands are separated, the next step in PCR involves hybridizing the separated strands with primers that flank the target sequence. The primers are then extended to form complementary copies of the target strands, and the cycle of denaturation, hybridization, and extension is repeated as many times as necessary to obtain the desired amount of amplified nucleic acid.

As noted above, the present invention provides PCR primers for the amplification of a target region of the $^G\gamma$-globin gene. These primers are complementary to sequences in conserved regions that flank the polymorphic region wherein the $^G\gamma$-globin sequence variations are located. For successful PCR amplification, the present primers are designed so that the position at which each primer hybridizes along a duplex sequence is such that an extension product synthesized from one primer, when separated from the template (complement), serves as a template for the extension of the other primer to yield an amplified segment of nucleic acid of defined length. Moreover, primers are provided that will bind preferentially to the $^G\gamma$-globin region under selective annealing conditions.

Template-dependent extension of primers in PCR is catalyzed by a polymerizing agent in the presence of adequate amounts of four deoxyribonucleoside triphosphates (dATP, dGTP, dCTP, and dTTP) in a reaction medium comprised of the appropriate salts, metal cations, and pH buffering system. Suitable polymerizing agents are enzymes known to catalyze template-dependent DNA synthesis. For example, if the template is RNA, a suitable polymerizing agent to convert the RNA into a complementary, copy-DNA (cDNA) sequence is reverse transcriptase (RT), such as avian myeloblastosis virus RT and *Thermus thermophilus* DNA polymerase, a thermostable DNA polymerase with reverse transcriptase activity marketed by PECI. Once the target for amplification is DNA, suitable polymerases include, for example, *E. coli* DNA polymerase I or its Klenow fragment, $T_4$ DNA polymerase, and Taq polymerase, a heat stable DNA polymerase isolated from *Thermus aquaticus* and commercially available from PECI. The latter enzyme is widely used in the amplification and sequencing of nucleic acids. The reaction conditions for using Taq polymerases are known in the art and are described in Gelfand, 1989, in *PCR Technology*, supra.

The PCR method can be performed in a step-wise fashion, where after each step new reagents are added, or in a fashion where all of the reagents are added simultaneously, or in a partial step-wise fashion, where fresh or different reagents are added after a given number of steps. For example, if strand separation is induced by heat, and the polymerase is heat-sensitive, then the polymerase has to be added after every round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the temperature of the reaction mixture is cycled through a denaturing region, a primer annealing region, and a reaction region. A machine specifically adapted for use with a thermostable enzyme is commercially available from PECI.

Those skilled in the art will also be aware of the problem of contamination of a PCR by the amplified nucleic acid from previous reactions. Methods to reduce this problem are provided in U.S. patent application Ser. No. 609,157, incorporated herein by reference.

Amplification of the DNA sequences of the alleles of the $^G\gamma$-globin gene is a useful, but not a necessary, step in determining the $^G\gamma$-globin genotype of an individual. Specific probe hybridization, however, is an important step in successful performance of the present methods. The sequence-specific, oligonucleotide probes of the present invention are designed to hybridize specifically with a particular variant segment of a $^G\gamma$-globin allele and to have destabilizing mismatches with the other variant sequences known for the particular segment and work equally well with amplified or unamplified genomic DNA. Under stringent hybridization conditions, the probes hybridize specifically only to exactly complementary sequences in the variant segment of the $^G\gamma$-globin alleles. These SSO probes allow for sequence specific hybridization and comprise a hybridizing region that is preferably in the range of 10 to 30 bases, more preferably 12 to 24 bases, in length.

The assay methods for detecting hybrids formed between SSO probes and nucleic acid sequences can require that the probes contain additional features in addition to the hybridizing region. For example, if the probe is first immobilized, as in the "reverse" dot blot format described below, the probe can also contain long stretches of poly-dT that can be fixed to a nylon support by irradiation, a technique described in more detail in PCT Patent Publication No. 89/11548, incorporated herein by reference.

The probes of the invention can be synthesized and labeled using the techniques described above for synthesizing oligonucleotides. For example, the probe may be labeled at the 5'-end with $^{32}P$ by incubating the probe with $^{32}P$-ATP and kinase. A suitable non-radioactive label for SSO probes is horseradish peroxidase (HRP). Methods for preparing and detecting probes containing this label are described in the Examples below and in U.S. Pat. Nos. 4,914,210, and 4,962,029; the latter patents are incorporated herein by reference. For additional information on the use of such labeled probes, see U.S. Pat. No. 4,789,630; Saiki et al., 1988, N. Eng. J. Med. 319:537–541; and Bugawan et al., 1988, *Bio/Technology* 6:943–947, each of which is incorporated herein by reference. Useful chromogens include red leuco dye and 3,3',5,5'-tetramethylbenzidine (TMB).

The probes of the invention can be used to identify the allelic sequences present in a sample by determining the SSO probes that bind to the $^G\gamma$-globin sequences present in the sample. Suitable assay methods for purposes of the present invention to detect hybrids formed between SSO probes and nucleic acid sequences in a sample are known in the art. For example, the detection can be accomplished using a dot blot format, as described in the Examples. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed with few probes, the dot blot format is quite useful.

An alternate method that is quite useful when large numbers of different probes are to be used is a "reverse" dot blot format, in which the amplified sequence contains a label, and the probe is bound to the solid support. In this format, the unlabeled SSO probes are bound to the membrane and exposed to the labeled sample under appropriately stringent hybridization conditions. Unhybridized labeled sample is then removed by washing under suitably stringent conditions, and the filter is then monitored for the presence of bound sequences.

Another suitable assay system is described in U.S. patent application Ser. No. 563,758, incorporated herein by reference, in which a labeled probe is added during the PCR amplification process. Any SSO probe which hybridizes to target DNA during each synthesis step is degraded by the 5' to 3' exonuclease activity of e.g., Taq polymerase. The degradation product from the probe is then detected. Thus, the presence of the breakdown product indicates that the hybridization between the SSO probe and the target DNA occurred.

Whatever the method for determining which SSO probes of the invention hybridize to $^G\gamma$-globin sequences in a sample, the central feature of the typing method involves the identification of the $^G\gamma$-globin alleles present in the sample by analyzing the pattern of binding of a panel of SSO probes. The specific application will determine which probes are used in a panel. For instance, if only the presence or absence of the C allele is of interest, a single probe specific for the C allele is adequate. The three possible genotypes of haploid cells (sperm cells, for example) can be determined using only two probes, one specific for each of two of the alleles. The third allele is then recognized by the absence of probe hybridization. In diploid cells, however, heterozygotes involving this third allele cannot be detected with only probes for the other two alleles. The feasibility of using single sperm for DNA typing is demonstrated in Li et al, 1988, *Nature* 335:441-417.

Another typing method useful for hapoid cells using only two probes is using probes that hybridize to only two out of the three alleles. This is achieved by using probes that are complementary to only part of the region where the HindIII site is located, as exemplified in Table II below. Only the ends of the hybridization regions of the probes extending into the HindIII site are shown; the rest of the probe is indicated by arrows. Probe 1, which is complementary to all of the HindIII site except for the last position where the T to G substitution defining the B allele occurs, will not bind to the C allele, but will bind to both the A and B allele. Similarly, probe 2 will hybridize to the A and C alleles, but not the B allele. Together, these probes are sufficient to determine the genotype of a haploid cell; both probes hybridizing indicates allele A is present, only probe 1 indicates allele B, and only probe 2 indicates allele C.

TABLE II

| HindIII | AAGCTT |
|---|---|
| Allele B | AAGCTG |
| Allele C | AATCTT |
| Probe 1 | ←AAGCT |
| Probe 2 | CTT→ |

DNA typing of $^G\gamma$-globin alleles is useful for many different purposes. For example, DNA typing methods now play a significant role in the important area of individual identification, whether for solving crimes, as when the identity of a criminal or victim is established by linking an individual with evidence left at the scene of a crime, or for solving other issues of a non-criminal nature, as when biological material is used to determine the maternity or paternity of an individual.

The DNA sequences provided above are an important aspect of the present invention. Although only one strand of the sequence is shown, those of skill in the art recognize that the other strand of the sequence can be inferred from the information depicted above. This information enables the construction of the probes and primers of the invention. Illustrative probes and primers of the invention are shown in the sequence listing. Tables VI and VII gives the corresponding designations for each sequence.

The present invention also relates to kits, multicontainer units comprising useful components for practicing the present method. A useful kit can contain SSO probes for the $^G\gamma$-globin gene. In some cases, the SSO probes may be fixed to an appropriate support membrane. The kit can also contain primers for PCR, as such primers are useful in the preferred embodiment of the invention. These primers will amplify a polymorphic region of the $^G\gamma$-globin gene. Other optional components of the kit include, for example, an agent to catalyze the synthesis of primer extension products, the substrate nucleoside triphosphates, means used to label (for example, an avidinenzyme conjugate and enzyme substrate and chromogen if the label is biotin), and the appropriate buffers for PCR or hybridization reactions. In addition to the above components, the kit can also contain instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

$^G\gamma$-globin Typing-Dot Blot Format

For typing samples with the panel of probes, 0.1 μg of human genomic DNA is amplified using reaction constituents as described in Saiki et al., 1988, *Science* 239:487-490, incorporated herein by reference. The primers, RS287 (SEQ ID NO:32) and RS288 (SEQ ID NO:33), are present in the reaction mixture at 0.25 μM. These primers produce a 345 base-pair (bp) fragment. Samples are amplified for 32 cycles using the reaction conditions described above. All samples are overlaid with 100 μl of high grade mineral oil (Sigma, St. Louis, Mo.) to prevent evaporation. One can also use the hot start methodology described in U.S. patent application Ser. No. 481,501, filed Feb. 16, 1990, and incorporated herein by reference, in performing the PCR amplification.

Before the first cycle, the sample is incubated at 72° C. for 30 seconds. The thermal profile for each of the 32 cycles comprises incubations at the following temperatures for the indicated times: 60 seconds at 94° C. (to denature the DNA strands), 30 seconds at 60° C. (to anneal the primers), and 30 seconds at 72° C. (to extend the primers). The PECI Thermal Cycler is programmed to incubate the samples at 72° C. for 10 minutes after the last cycle to ensure that the final extension is complete.

After amplification, a small portion of the amplified DNA is denatured and applied to a series of nylon filters; each filter is then hybridized to one of the labelled probes. Each of the SSO probes SN27 (SEQ ID NO:1), SN26 (SEQ ID NO:18), and RS339 (SEQ ID NO:23) is covalently conjugated to horseradish peroxidase (HRP) and provides a means of nonisotopic detection in the presence of a chromogenic or chemiluminescent substrate.

Thus, 5 μl of each amplified DNA sample are mixed with 100 μl of a mixture composed of 0.4M NaOH and 25 mM EDTA, and the resulting mixture is applied to 5 BioDyne B nylon filters (Pall Corp., Glen Cove, N.Y.) using a dot-blot manifold (Bio Rad, Richmond, Calif.). The filters are rinsed with a mixture of 10 mM Tris-HCl and 0.1 mM EDTA, at pH 8.0, and dried on Whatman 3MM paper. The DNA is immobilized on the nylon filter by ultraviolet irradiation at a flux of 55 mJ/cm$^2$ with a Stratalinker ™ (Stratagene, La Jolla, Calif.). UV light box.

All filters are hybridized in 2X SSPE (saline sodium phosphate EDTA), 5X Denhardt's solution, and 0.5% SDS with 2 pmoles of HRP-SSO probe per 5 ml of hybridization solution for 15 min. at 42° C. Horseradish peroxidase conjugated oligonucleotides are prepared as described by Levenson and Chang, 1989, in *PCR Protocols: A Guide to Methods and Applications*, Innis et al., eds., Academic Press. San Diego):92–112, incorporated herein by reference, and Saiki et al., 1988, *N. Eng. J. Med.* 319:537–541. Filters for each probe are washed in 10 ml of the SSPE solution at 55° C.

After washing, filters to be developed with a chromogenic dye substrate are rinsed in 100 mM sodium citrate, pH 5.0, then placed in 100 mM sodium citrate, pH 5.0, containing 0.1 mg/ml of 3,3',5,5'-tetramethylbenzidine per milliliter (Fluka) and 0.0015 percent hydrogen peroxide, and incubated with gentle agitation for 10 to 30 minutes at room temperature. Developed filters are rinsed in water and immediately photographed. The TMB detection system is prepared and used substantially as described in AmpliType ® DQalpha DNA typing kit marketed by PECI. In another embodiment, filters are developed with the chemiluminescent detection system (ECL; Amersham, Arlington Heights, Ill.). Filters are rinsed in PBS for 5 minutes and placed in the ECL solution for 1 minute with gentle agitation. Filters are then exposed to X-ray film at room temperature for 1 to 5 minutes.

EXAMPLE 2

$^G\gamma$-globin Typing-Reverse Dot Blot Format

In this embodiment of the invention, the $^G\gamma$-globin probes are fixed to a membrane, and the amplified target DNA is hybridized to the membrane-bound probe as described in Saiki et al., 1989, *Proc. Natl. Acad. Sci.* 86:6230–6234 and in the AmpliType ® DQalpha DNA typing kit marketed by PECI. The set of typing probes is designed so that each probe will hybridize to a specific target sequence at the same temperature and salt concentration (and stay hybridized under the same wash conditions) as all other probes in the set. The PCR primers used in the amplification are biotinylated, as described in Levenson and Chang, 1989, supra, so that any amplified DNA that hybridizes to the membrane-bound probes can be easily detected.

In one embodiment, detection is carried out by reacting streptavidin conjugated horseradish peroxidase (SA-HRP) with any biotinylated, amplified DNA hybridized to the membrane-bound probe. The HRP thus becomes bound, through the SA-biotin interaction, to the amplified DNA and can be used to generate a signal by a variety of well known means, such as the generation of a colored compound, e.g., by the oxidation of tetramethylbenzidine (see U.S. Pat. No. 4,789,630).

Although the probes can be fixed to the membrane by any means, a preferred method involves "tailing" an oligonucleotide probe about 13 to 25 nucleotides in length (the hybridizing region) with a much longer sequence of poly-dT. The resulting poly-dT "tail" can then be reacted with amine groups on a nylon membrane to fix the probe covalently to the membrane. This reaction can be facilitated by UV irradiation.

Terminal deoxyribonucleotidyl transferase (TdT, Ratliff Biochemicals; for the reactions below assume a concentration of abut 120 Units/μl, which is 100 pmole/μl) can be used to create a poly-dT tail on a probe, although one can also synthesize the tailed probe on a commercially available DNA synthesizer. When one uses a DNA synthesizer to make the tailed probe, however, one should place the tail on the 5' end of the probe, so that undesired premature chain termination occurs primarily in the tail region.

TdT reactions should be carried out in a volume of about 100 μl containing 1X TdT salts, 200 pmole of oligonucleotide, 800 μM dTT, and 60 units of TdT. 10X TdT salts is 1,000 mM K-cacodylate, 10 mM CoCl$_2$, 2 mM dithiothreitol, 250 mM Tris-Cl, pH 7.6, and is prepared as described by Roychoudhury and Wu, *Meth. Enzymol.* 65: 43–62, incorporated herein by reference. A 10X stock solution of 8 mM dTTP can be prepared (neutralized to pH 7 with NaOH) for convenience.

The TdT reaction should be carried out at 37° C. for two hours and then stopped by the addition of 100 μl of 10 mM EDTA, pH 8. The final concentration of tailed oligonucleotide is 1 μM (1 pmole/μl), and the length of the homopolymer tail is about 400 residues. Tail length can be changed by adjusting the molar ratio of dTTP to oligonucleotide. The tailed probes can be stored at −20° C. until use.

Two types of nylon membrane are preferred for the reverse dot blot format: Biodyne ™ nylon membrane, 0.45 micron pore size, manufactured by Pall; and Biotrans ™ nylon membrane, 0.45 micron pore size, manufactured by ICN. The probes can be spotted onto the membrane very conveniently with the Bio-Dot ™ dot blot apparatus manufactured by BioRad. Each probe is spotted onto a unique, discrete location onto the membrane. About 2 to 10 picomoles of each tailed probe is premixed with 50–100 μl of TE buffer before application to the dot blot apparatus. After dot blotting, the membrane is briefly placed on absorbent paper to draw off excess liquid.

The membrane is then placed inside a UV light box, such as the Stratalinker ™ light box manufactured by Stratagene and exposed to 50 to 60 millijoules/cm$^2$ of flux at 254 nm to fix the tailed probe to the nylon membrane. After a brief rinse (for about 15 minutes in hybridization solution) to remove unbound probe, the membrane is then ready for hybridization with biotinylated PCR product. One-half to one picomole (one-quarter to one-half of a typical, 100 μl PCR mixture) of PCR product is added to each probe panel for hybridization. About 50 μl of SA-HRP, commercially available from PECI, can be added at this time for convenience, but better signals will result if a separate SA-HRP incubation and wash, at room temperature, is performed after the hybridization step but before the stringency wash.

Hybridization is typically carried out at 55° C. for 30 minutes in a water bath and with hybridization buffer composed of 0.5% SDS and 5X SSPE. Biotin binding is carried out in the hybridization buffer for 10 minutes at 55° C. Stringency washing is carried out at 55° C. for 10 minutes in a water bath and with wash solution composed of 0.1% SDS and 2.5X SSPE. A post-wash of 1X PBS at room temperature for 30 minutes can enhance signal quality.

The hybridization region of the biotinylated primers for the reverse dot blot method are the same as the primers of Example 1. Note that one or both of the primers can be biotinylated in an amplification and that the primers can be used for amplification with any detection format.

The hybridizing regions of the tailed probes and biotinylated primers for use in the reverse dot blot method are the same as the probes and primers of Example 1.

EXAMPLE 3

Frequencies of the $^G\gamma$-globin Alleles

Samples from three different populations were typed at the $^G\gamma$-globin locus: 20 from a Caucasian population, fourteen from a Hispanic population, and 34 from a Black population. The typing at the $^G\gamma$-globin locus was done simultaneously with typing at LDL, D7S8, and Gc loci. In addition, primers for amplifying a region of the DQ locus were added during the amplification step. The results of the $^G\gamma$-globin DNA typing are shown below.

Amplification was done substantially as in Example 1 with the modifications described below. The amplification reagents "premix" solution used comprised the following: 200 μl of 10X Taq buffer; 200 μl of dNTP's (8 mM solution); 50 μl each of primers (10 μM solution) RS287 (SEQ ID NO:32), RS288 (SEQ ID NO:33), SN58, SN59, RS175, RS176, RS227, RS228, RS134, and RS135; 1,084 μl of H₂O; and 16 μl of Taq polymerase (5 units/μl solution). The primers other than RS287 and RS288 were for amplification of regions of the other loci. About 100 ng of genomic DNA were added to 100 μl of premix solution and amplified using the temperature profile of Example 1.

The probes used for typing at the $^G\gamma$-globin locus were SN27 (SEQ ID NO:1), SN26 (SEQ ID NO:18), RS339 (SEQ ID NO:23) for the A, B, and C alleles, respectively. The probes designated RS179, RS180, RS229, RS230, RS318, RS319, and RS320 were used for typing at the other three loci. The reverse dot-blot detection scheme was used substantially as described in Example 2, except that hybridization was carried out for 15 minutes at 55° C. and the subsequent stringency wash was for 10 minutes at 55° C. Filters were developed substantially as in Example 1, but with 2 mg/ml TMB and 3% H₂O₂.

Allele and genotype frequency estimates for the three populations are given in Table II below. Numbers may not add to 1 due to round-off errors. The frequency of the C allele in the Black population is substantial. The usefulness of the $^G\gamma$-globin locus for individual identification is greatly enhanced by the discovery of a third allele present in the Black population at relatively high frequencies.

TABLE III

| Population | A | B | C | AA | AB | AC | BB | BC | CC |
|---|---|---|---|---|---|---|---|---|---|
| Caucasian | .60 | .375 | .025 | .40 | .15 | 0 | .4 | .05 | 0 |
| Hispanic | .36 | .54 | .10 | .14 | .29 | .14 | .36 | .07 | 0 |

TABLE III-continued

| Population | A | B | C | AA | AB | AC | BB | BC | CC |
|---|---|---|---|---|---|---|---|---|---|
| Black | .38 | .29 | .32 | .12 | .26 | .26 | .09 | .18 | .12 |

EXAMPLE 4

Polymarker Kit

In this embodiment, the $^G\gamma$-globin typing system is used in the Polymarker ™ kit produced by Cetus Corporation as one part of a six gene typing system with particular application in the field of forensics. The DNA type of a suspected individual is compared to the type determined from the sample of unknown origin to determine if the sample could have originated from the suspect. The increased power of discrimination that comes from typing multiple loci and as many alleles at each loci as conveniently possible increases the effectiveness of the test in the forensic setting.

The protocol is substantially as in Examples 2 and 3, above, with some differences noted as follows. The concentrations in the reaction mixture are 0.25 μM for each of the primers, 0.2 mM for each of the dNTPs, and 4 units per reaction of Taq polymerase. The 32 cycles of amplification (94° C., 1 minute; 60° C., 30 seconds; 72° C., 30 seconds) are followed by a final 7 minute extension at 72° C.

In this embodiment, six loci are simultaneously typed. The designation and sequence identification numbers of the primers and probes for all the loci used are listed below. The probes are fixed to a Nylon membrane (Pall Biodyne B ™).

TABLE IV

| | Primer Pairs | |
|---|---|---|
| Gene | Primer 1 | Primer 2 |
| $^G\gamma$-globin | RS287 (SEQ ID NO: 32) | RS412 (SEQ ID NO: 33) |
| LDL$^r$ | RS175 (SEQ ID NO: 36) | RS176 (SEQ ID NO: 37) |
| DQα | RS134 (SEQ ID NO: 38) | RS135 (SEQ ID NO: 39) |
| Glycophorin A | RS362 (SEQ ID NO: 40) | RS364 (SEQ ID NO: 41) |
| D7S8 | RS227 (SEQ ID NO: 42) | RS383 (SEQ ID NO: 43) |
| Gc | SN58 (SEQ ID NO: 44) | SN59 (SEQ ID NO: 45) |

TABLE V

| | DNA Probe Strips | | |
|---|---|---|---|
| Gene | Allele | T-Tail | Seq ID No. of Hybridization Region |
| $^G\gamma$-globin | A | 200T | 1 |
| | B | 100T | 22 |
| | C | 100T | 30 |
| LDL$^r$ | A | 200T | 46 |
| | B | 100T | 47 |
| Glycophorin (M) | A | 100T | 48 |
| A (N) | B | 100T | 49 |
| D7S8 | A | 100T | 50 |
| | B | 100T | 51 |
| Gc (2) | A | 100T | 52 |
| (1F) | B | 100T | 53 |
| (1S) | C | 100T | 54 |
| DQα All Probe | S | 200T | 55 |

EXAMPLE 5

Primers and Probes

Those of skill in the art recognize that primers and probes useful in the present methods can vary somewhat in length and therefore in sequence. Tables VI and VII below show a variety of illustrative primers and probes useful in the present method.

TABLE VI

| Allele | A | | | | | | | | |
|---|---|---|---|---|---|---|---|---|---|
| Probe | SN27 | VP10 | VP11 | VP23 | VP43 | VP44 | VP50 | VP51 | VP52 |
| Seq. ID No. | 1 | 2 | 3 | 4 | 5 | 6 | 7 | 8 | 9 |
| Allele | | | | | | | | | B |
| Probe | VP61 | VP62 | VP63 | VP64 | VP65 | VP66 | VP67 | VP68 | SN26 |
| Seq. ID No. | 10 | 11 | 12 | 13 | 14 | 15 | 16 | 17 | 18 |
| Allele | | | | | C | | | | |
| Probe | VP16 | VP08 | VP49 | VP59 | RS339 | VP12 | VP17 | VP24 | VP40 |
| Seq. ID No. | 19 | 20 | 21 | 22 | 23 | 24 | 25 | 26 | 27 |
| Allele | | | | | | | | | |
| Probe | VP41 | VP42 | VP60 | | | | | | |
| Seq. ID No. | 28 | 29 | 30 | | | | | | |

TABLE VII

| Primers | Seq. ID. No. |
|---|---|
| RS173 | 31 |
| RS287 | 32 |

TABLE VII-continued

| Primers | Seq. ID. No. |
|---|---|
| RS288 | 33 |
| RS410 | 34 |
| RS412 | 35 |

---

We claim:

1. A process for detecting the presence of a variant sequence of the $^G\gamma$-globin locus which defines a C allele in a sample containing $^G\gamma$-globin locus nucleic acids comprising:
   (a) mixing said nucleic acid with a sequence-specific oligonucleotide (SSO) probe complementary to said variant sequence defining said C allele under conditions wherein said SSO probe binds to said nucleic acid to form a stable hybrid duplex only if said SSO probe is exactly complementary to said nucleic acid; and
   (b) detecting hybrids formed between said nucleic acid and said SSO probe.

2. A process for determining an individual's $^G\gamma$-globin locus genotype from a sample containing $^G\gamma$-globin locus nucleic acid obtained from said individual, said process comprising:
   (a) mixing said nucleic acid with a panel of at least two sequence-specific oligonucleotide (SSO) probes, said panel comprising at least an SSO probe with a hybridizing region complementary to a variant sequence defining a C allele and a SSO probe with a hybridizing region complementary to either a variant sequence defining an A allele or a variant sequence defining a B allele, under conditions wherein said SSO probes bind to said nucleic acid to form stable hybrid duplexes only if said SSO probes are exactly complementary to said nucleic acid; and
   (b) detecting hybrids formed between said nucleic acid and said SSO probes.

3. The process of claim 2, wherein said panel of SSO probes comprises SSO probes to said A, B, and C alleles, wherein the hybridization region of each SSO probe is a sequence of between 12 and 24 nucleotides which is exactly complementary to one of said alleles.

4. The process of claim 2, wherein said panel of SSO probes comprises an SSO probe with the hybridization region SEQ ID NO: 1, an SSO probe with the hybridization region SEQ ID NO: 18, and an SSO probe with the hybridization region SEQ ID NO: 23.

5. The process of claim 2, wherein said $^G\gamma$-globin locus nucleic acid is first amplified and said panel of SSO is mixed with the amplified nucleic acid.

6. The process of claim 5, wherein the amplification is achieved with a polymerase chain reaction.

7. The process of claim 5, wherein said panel of SSO probes comprises SSO probes to said A, B, and C alleles, wherein the hybridization region of each SSO probe is a sequence of between 12 and 24 nucleotides which is exactly complementary to one of said alleles.

8. The process of claim 5, wherein said panel of SSO probes comprises an SSO probe with the hybridization region SEQ ID NO: 1, an SSO probe with the hybridization region SEQ ID NO: 18, and an SSO probe with the hybridization region SEQ ID NO: 23.

9. The process of claim 6, wherein said polymerase chain reaction is carried out in the presence of a primer with the hybridization region SEQ ID NO: 32 and a primer with the hybridization region SEQ ID NO: 33.

10. A method for providing forensic evidence concerning the derivation of a sample, wherein said method comprises:
    (a) using the process of claim 2 to determine the genotype at the $^G\gamma$-globin locus of both said sample and a suspected individual, and
    (b) comparing the genotypes obtained.

* * * * *

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO:1:

CACACCAAGC TTCCAC        1 6

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO:2:

CACACCAAGC TTCCACC        1 7

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO:3:

TACACACCAA GCTTCCA        1 7

( 2 ) INFORMATION FOR SEQ ID NO:4:

( i ) SEQUENCE CHARACTERISTICS:
    ( A ) LENGTH: 18 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO:4:

AACACACCAA GCTTCCAC     18

( 2 ) INFORMATION FOR SEQ ID NO:5:

( i ) SEQUENCE CHARACTERISTICS:
    ( A ) LENGTH: 16 base pairs
    ( B ) TYPE: nucleic acid
    ( C ) STRANDEDNESS: single stranded
    ( D ) TOPOLOGY: linear ( i i ) MOLECULE TYPE:

( x i ) SEQUENCE DESCRIPTION: SEQ ID NO:5:

CACCAAGCTT CCACCC     16

( 2 ) INFORMATION FOR SEQ ID NO: 6:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 6:

ATAACTACAC ACCAAGC     17

( 2 ) INFORMATION FOR SEQ ID NO: 7:

( i ) SEQUENCE CHARACTERISTICS:
    ( A ) LENGTH: 16 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 7:

ACACCAAGCT TCCACC     16

( 2 ) INFORMATION FOR SEQ ID NO: 8:

( i ) SEQUENCE CHARACTERISTICS:
    ( A ) LENGTH: 16 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 8:

CAAGCTTCCA CCCAGA     16

( 2 ) INFORMATION FOR SEQ ID NO: 9:

( i ) SEQUENCE CHARACTERISTICS:
    ( A ) LENGTH: 16 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 9:

CACCAAGCTT CCACCT         16

( 2 ) INFORMATION FOR SEQ ID NO: 10:

( i ) SEQUENCE CHARACTERISTICS:
    ( A ) LENGTH: 16 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 10:

CACACCAAGC TTCCAC         16

( 2 ) INFORMATION FOR SEQ ID NO: 11:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 11:

CACAACAAGC TTCCACC        17

( 2 ) INFORMATION FOR SEQ ID NO: 12:

( i ) SEQUENCE CHARACTERISTICS:
    ( A ) LENGTH: 18 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 12:

CACACCAAAC TTCCACCC       18

( 2 ) INFORMATION FOR SEQ ID NO: 13:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 13:

CACATCAAGC TTCCACC        17

( 2 ) INFORMATION FOR SEQ ID NO: 14:

( i ) SEQUENCE CHARACTERISTICS:
    ( A ) LENGTH: 18 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 14:

CACAACAAGC TTCCACCC       18

( 2 ) INFORMATION FOR SEQ ID NO: 15:

( i ) SEQUENCE CHARACTERISTICS:
    ( A ) LENGTH: 20 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 15:

TACACAACAA GCTTCCACCC    20

( 2 ) INFORMATION FOR SEQ ID NO: 16:

( i ) SEQUENCE CHARACTERISTICS:
    ( A ) LENGTH: 20 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 16:

TACACACAAA GCTTCCACCC    20

( 2 ) INFORMATION FOR SEQ ID NO: 17:

( i ) SEQUENCE CHARACTERISTICS:
    ( A ) LENGTH: 20 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 17:

TACACACCAG GCTTCCACCC    20

( 2 ) INFORMATION FOR SEQ ID NO: 18:

( i ) SEQUENCE CHARACTERISTICS:
    ( A ) LENGTH: 16 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 18:

CACACCCAGC TTCCAC    16

( 2 ) INFORMATION FOR SEQ ID NO: 19:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 19:

TACACACCCA GCTTCCA    17

( 2 ) INFORMATION FOR SEQ ID NO: 20:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 20:

CACACCCAGC TTCCACC           17

( 2 ) INFORMATION FOR SEQ ID NO: 21:

( i ) SEQUENCE CHARACTERISTICS:
      ( A ) LENGTH: 18 base pairs
      ( B ) TYPE: nucleic acid
      ( C ) STRANDEDNESS: single stranded
      ( D ) TOPOLOGY: linear ( i i ) MOLECULE TYPE: Other nucleic acid ( x i ) SEQUENCE DESCRIPTION: SEQ ID NO: 21:

TACACACCCA GCTTCCAC          18

( 2 ) INFORMATION FOR SEQ ID NO: 22:

( i ) SEQUENCE CHARACTERISTICS:
      ( A ) LENGTH: 16 base pairs
      ( B ) TYPE: nucleic acid
      ( C ) STRANDEDNESS: single stranded
      ( D ) TOPOLOGY: linear ( i i ) MOLECULE TYPE: Other nucleic acid ( x i ) SEQUENCE DESCRIPTION: SEQ ID NO: 22:

ACACCCAGCT TCCACC          16

( 2 ) INFORMATION FOR SEQ ID NO: 23:

( i ) SEQUENCE CHARACTERISTICS:
      ( A ) LENGTH: 16 base pairs
      ( B ) TYPE: nucleic acid
      ( C ) STRANDEDNESS: single stranded
      ( D ) TOPOLOGY: linear ( i i ) MOLECULE TYPE: Other nucleic acid ( x i ) SEQUENCE DESCRIPTION: SEQ ID NO: 23:

CACACCAAGA TTCCAC          16

( 2 ) INFORMATION FOR SEQ ID NO: 24:

( i ) SEQUENCE CHARACTERISTICS:
      ( A ) LENGTH: 17 base pairs
      ( B ) TYPE: nucleic acid
      ( C ) STRANDEDNESS: single stranded
      ( D ) TOPOLOGY: linear ( i i ) MOLECULE TYPE: Other nucleic acid ( x i ) SEQUENCE DESCRIPTION: SEQ ID NO: 24:

CACACCAAGA TTCCACC          17

( 2 ) INFORMATION FOR SEQ ID NO: 25:

( i ) SEQUENCE CHARACTERISTICS:
      ( A ) LENGTH: 17 base pairs
      ( B ) TYPE: nucleic acid
      ( C ) STRANDEDNESS: single stranded
      ( D ) TOPOLOGY: linear ( i i ) MOLECULE TYPE: Other nucleic acid ( x i ) SEQUENCE DESCRIPTION: SEQ ID NO: 25:

TACACACCAA GATTCCA          17

( 2 ) INFORMATION FOR SEQ ID NO: 26:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 26:

AACACACCAA GATTCCA    17

( 2 ) INFORMATION FOR SEQ ID NO: 27:

( i ) SEQUENCE CHARACTERISTICS:
    ( A ) LENGTH: 18 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 27:

TACACACCAA GATTCCAC    18

( 2 ) INFORMATION FOR SEQ ID NO: 28:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 28:

GTGGAATCTT GGTGTGT    17

( 2 ) INFORMATION FOR SEQ ID NO: 29:

( i ) SEQUENCE CHARACTERISTICS:
    ( A ) LENGTH: 17 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 29:

GGTGGAATCT TGGTGTG    17

( 2 ) INFORMATION FOR SEQ ID NO: 30:

( i ) SEQUENCE CHARACTERISTICS:
    ( A ) LENGTH: 18 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 30:

GGTGGAATCT TGGTGTGT    18

( 2 ) INFORMATION FOR SEQ ID NO: 31:

( i ) SEQUENCE CHARACTERISTICS:
    ( A ) LENGTH: 20 base pairs
    ( B ) TYPE: nucleic acid
    ( C ) STRANDEDNESS: single stranded
    ( D ) TOPOLOGY: linear ( i i ) MOLECULE TYPE: Other nucleic acid ( x i ) SEQUENCE DESCRIPTION: SEQ ID NO: 31:

AGTGACTAGT GCTGCAAGAA                    20

( 2 ) INFORMATION FOR SEQ ID NO: 32:

( i ) SEQUENCE CHARACTERISTICS:
        ( A ) LENGTH: 24 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 32:

GGCCAGTGAC TAGTGCTGCA AGAA                    24

( 2 ) INFORMATION FOR SEQ ID NO: 33:

( i ) SEQUENCE CHARACTERISTICS:
        ( A ) LENGTH: 26 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 33:

TGAAAGCTCT GCATCATGGG CAGTGA                    26

( 2 ) INFORMATION FOR SEQ ID NO: 34:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 34:

GGACAGGGCA CTGGCCACTC                    20

( 2 ) INFORMATION FOR SEQ ID NO: 35:

( i ) SEQUENCE CHARACTERISTICS:
        ( A ) LENGTH: 28 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 35:

AGACAATAAA GATGAACCCA TAGTGAGC                    28

( 2 ) INFORMATION FOR SEQ ID NO: 36:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 36:

AGTGCCAACC GCCTCACAGG                    20

( 2 ) INFORMATION FOR SEQ ID NO: 37:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 37:

CCTCTCACAC CAGTTCACTC           20

( 2 ) INFORMATION FOR SEQ ID NO: 38:

( i ) SEQUENCE CHARACTERISTICS:
        ( A ) LENGTH: 26 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 38:

GTGCTGCAGG TGTAAACTTG TACCAG       26

( 2 ) INFORMATION FOR SEQ ID NO: 39:

( i ) SEQUENCE CHARACTERISTICS:
        ( A ) LENGTH: 28 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 39:

CACGGATCCG GTAGCAGCGG TAGAGTTG     28

( 2 ) INFORMATION FOR SEQ ID NO: 40:

( i ) SEQUENCE CHARACTERISTICS:
        ( A ) LENGTH: 25 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 40:

GGATGTGAGG AATTTGTCTT TTGCA       25

( 2 ) INFORMATION FOR SEQ ID NO: 41:

( i ) SEQUENCE CHARACTERISTICS:
        ( A ) LENGTH: 25 base pairs
        ( B ) TYPE: nucleic acid
        ( C ) STRANDEDNESS: single stranded
        ( D ) TOPOLOGY: linear ( i i ) MOLECULE TYPE: Other nucleic acid ( x i ) SEQUENCE DESCRIPTION: SEQ ID NO: 41:

CCATTTGTCT GTGATGAGAT GTAAC       25

( 2 ) INFORMATION FOR SEQ ID NO: 42:

( i ) SEQUENCE CHARACTERISTICS:
        ( A ) LENGTH: 21 base pairs
        ( B ) TYPE: nucleic acid
        ( C ) STRANDEDNESS: single stranded (D) TOPOLOGY: linear (i i) MOLECULE TYPE: Other nucleic acid (x i) SEQUENCE DESCRIPTION: SEQ ID NO: 42:

CTAGGGATGT TCCTGTCTCA G 21

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single stranded
        (D) TOPOLOGY: linear (i i) MOLECULE TYPE: Other nucleic acid (x i) SEQUENCE DESCRIPTION: SEQ ID NO: 43:

TGCCAAGCCC TGTTCTGCGA 20

(2) INFORMATION FOR SEQ ID NO: 44:

(i) SEQUENCE CHARACTERISTICS:
        (A) LENGTH: 27 base pairs
        (B) TYPE: nucleic acid
        (C) STRANDEDNESS: single stranded
        (D) TOPOLOGY: linear (i i) MOLECULE TYPE: Other nucleic acid (x i) SEQUENCE DESCRIPTION: SEQ ID NO: 44:

CTGGCAGAGC GACTAAAAGC AAAATTG 27

(2) INFORMATION FOR SEQ ID NO: 45:

(i) SEQUENCE CHARACTERISTICS:
        (A) LENGTH: 30 base pairs
        (B) TYPE: nucleic acid
        (C) STRANDEDNESS: single stranded
        (D) TOPOLOGY: linear (i i) MOLECULE TYPE: Other nucleic acid (x i) SEQUENCE DESCRIPTION: SEQ ID NO: 45:

ATCAATCTCT GAATCACAGT AAAGAGGAGG 30

(2) INFORMATION FOR SEQ ID NO: 46:

(i) SEQUENCE CHARACTERISTICS:
        (A) LENGTH: 20 base pairs
        (B) TYPE: nucleic acid
        (C) STRANDEDNESS: single stranded
        (D) TOPOLOGY: linear (i i) MOLECULE TYPE: Other nucleic acid (x i) SEQUENCE DESCRIPTION: SEQ ID NO: 46:

AGGATATGGT CCTCTTCCAC 20

(2) INFORMATION FOR SEQ ID NO: 47:

(i) SEQUENCE CHARACTERISTICS:
        (A) LENGTH: 19 base pairs
        (B) TYPE: nucleic acid
        (C) STRANDEDNESS: single stranded
        (D) TOPOLOGY: linear (i i) MOLECULE TYPE: Other nucleic acid (x i) SEQUENCE DESCRIPTION: SEQ ID NO: 47:

TGGAAGAGAA CCATATCCT 19

( 2 ) INFORMATION FOR SEQ ID NO: 48:

( i ) SEQUENCE CHARACTERISTICS:
( A ) LENGTH: 19 base pairs
( B ) TYPE: nucleic acid
( C ) STRANDEDNESS: single stranded
( D ) TOPOLOGY: linear ( i i ) MOLECULE TYPE: Other nucleic acid ( x i ) SEQUENCE DESCRIPTION: SEQ ID NO: 48:

CATTGCCACA CCAGTGGTA                    19

( 2 ) INFORMATION FOR SEQ ID NO: 49:

( i ) SEQUENCE CHARACTERISTICS:
( A ) LENGTH: 19 base pairs
( B ) TYPE: nucleic acid
( C ) STRANDEDNESS: single stranded
( D ) TOPOLOGY: linear ( i i ) MOLECULE TYPE: Other nucleic acid ( x i ) SEQUENCE DESCRIPTION: SEQ ID NO: 49:

TACCACTGAG GTGGCAATG                    19

( 2 ) INFORMATION FOR SEQ ID NO: 50:

( i ) SEQUENCE CHARACTERISTICS:
( A ) LENGTH: 16 base pairs
( B ) TYPE: nucleic acid
( C ) STRANDEDNESS: single stranded
( D ) TOPOLOGY: linear ( i i ) MOLECULE TYPE: Other nucleic acid ( x i ) SEQUENCE DESCRIPTION: SEQ ID NO: 50:

CTTTCCCGGA ATGCTG                       16

( 2 ) INFORMATION FOR SEQ ID NO: 51:

( i ) SEQUENCE CHARACTERISTICS:
( A ) LENGTH: 17 base pairs
( B ) TYPE: nucleic acid
( C ) STRANDEDNESS: single stranded
( D ) TOPOLOGY: linear ( i i ) MOLECULE TYPE: Other nucleic acid ( x i ) SEQUENCE DESCRIPTION: SEQ ID NO: 51:

CAGCATTCCA GGAAAGG                      17

( 2 ) INFORMATION FOR SEQ ID NO: 52:

( i ) SEQUENCE CHARACTERISTICS:
( A ) LENGTH: 16 base pairs
( B ) TYPE: nucleic acid
( C ) STRANDEDNESS: single stranded
( D ) TOPOLOGY: linear ( i i ) MOLECULE TYPE: Other nucleic acid ( x i ) SEQUENCE DESCRIPTION: SEQ ID NO: 52:

GATGACACAC CCAAGG                       16

( 2 ) INFORMATION FOR SEQ ID NO: 53:

( i ) SEQUENCE CHARACTERISTICS:
( A ) LENGTH: 16 base pairs
( B ) TYPE: nucleic acid (C) STRANDEDNESS: single stranded
(D) TOPOLOGY: linear (ii) MOLECULE TYPE: Other nucleic acid (xi) SEQUENCE DESCRIPTION: SEQ ID NO: 53:

GATGCCAAAC CCACGG 16

(2) INFORMATION FOR SEQ ID NO: 54:

(i) SEQUENCE CHARACTERISTICS:
(A) LENGTH: 18 base pairs
(B) TYPE: nucleic acid
(C) STRANDEDNESS: single stranded
(D) TOPOLOGY: linear (ii) MOLECULE TYPE: Other nucleic acid (xi) SEQUENCE DESCRIPTION: SEQ ID NO: 54:

GGCCGTGGGG GTGGCCTC 18

(2) INFORMATION FOR SEQ ID NO: 55:

(i) SEQUENCE CHARACTERISTICS:
(A) LENGTH: 35 base pairs
(B) TYPE: nucleic acid
(C) STRANDEDNESS: single stranded
(D) TOPOLOGY: linear (ii) MOLECULE TYPE: Other nucleic acid (xi) SEQUENCE DESCRIPTION: SEQ ID NO: 55:

TTCTACGTGG ACCTGGAGAG GAAGGAGACT GCCTG 35

(2) INFORMATION FOR SEQ ID NO: 56:

(i) SEQUENCE CHARACTERISTICS:
(A) LENGTH: 15 base pairs
(B) TYPE: nucleic acid
(C) STRANDEDNESS: Single
(D) TOPOLOGY: linear (ii) MOLECULE TYPE: Other nucleic acid (xi) SEQUENCE DESCRIPTION: SEQ ID NO: 56:

AAGCTTGGTG TGTAG 15

(2) INFORMATION FOR SEQ ID NO: 57:

(i) SEQUENCE CHARACTERISTICS:
(A) LENGTH: 15 base pairs
(B) TYPE: nucleic acid
(C) STRANDEDNESS: Single
(D) TOPOLOGY: linear (ii) MOLECULE TYPE: Other nucleic acid (xi) SEQUENCE DESCRIPTION: SEQ ID NO: 57:

AAGCTGGGTG TGTAG 15

(2) INFORMATION FOR SEQ ID NO: 58:

(i) SEQUENCE CHARACTERISTICS:
(A) LENGTH: 15 base pairs
(B) TYPE: nucleic acid
(C) STRANDEDNESS: Single
(D) TOPOLOGY: linear (ii) MOLECULE TYPE: Other nucleic acid (xi) SEQUENCE DESCRIPTION: SEQ ID NO: 58:

```
AATCTTGGTG TGTAA                    15
```